United States Patent [19]

Domes et al.

[11] Patent Number: 4,904,348
[45] Date of Patent: Feb. 27, 1990

[54] METHOD FOR THE PRODUCTION OF DENTAL SPARE PARTS, SUCH AS TOOTH CROWNS- AND BRIDGES, BY MEANS OF SPARK EROSION

[75] Inventors: Anton Domes, Bruchköbel; Alfred Höritzer, Stuttgart, both of Fed. Rep. of Germany

[73] Assignee: Heraeus Edelmetalle GmbH, Hanau, Fed. Rep. of Germany

[21] Appl. No.: 255,622

[22] Filed: Oct. 11, 1988

[30] Foreign Application Priority Data

Oct. 21, 1987 [DE] Fed. Rep. of Germany ....... 3735558

[51] Int. Cl.$^4$ .............................................. C25D 1/00
[52] U.S. Cl. .................................... 204/4; 204/129.1; 249/54; 264/19
[58] Field of Search ........................ 204/3, 4, 6, 129.1; 264/19; 249/54

[56] References Cited

U.S. PATENT DOCUMENTS

| | | | |
|---|---|---|---|
| 3,649,474 | 3/1972 | Blakeslee et al. | 204/6 |
| 3,689,729 | 9/1972 | Neward et al. | 204/129.1 |
| 4,169,017 | 9/1979 | Burkey et al. | 204/4 |
| 4,734,173 | 3/1988 | Walter et al. | 204/129.1 |

FOREIGN PATENT DOCUMENTS 3320902 9/1986 Fed. Rep. of Germany .

OTHER PUBLICATIONS

"Herstellung einer Metallhülsenkrone aus Vollmaterial mit Hilfe der Funkenerosion", from Deutsche Zahnärztliche Z 41, 525–526 (1986).

Primary Examiner—Jan H. Silbaugh
Assistant Examiner—Christopher A. Fiorilla
Attorney, Agent, or Firm—Felfe & Lynch

[57] ABSTRACT

Positive wax models are disposed on carriers in a casting frame so that the widest cross sections are in a common plane, vertical fitting pins are provided, and the frame is filled with silicone to the level of the plane to form a first model. The surface is then coated with silver, electroplated with copper, and reinforced with synthetic resin to form a first electrode, which is removed from the first model. The first model is likewise removed from the frame and oriented by means of the fitting pins in a casting frame filled with hardening carrier mass to the plane of the widest cross sections. The carriers and molding mass are then removed to form a second model. The surface of the second model is then coated with silver, electroplated with copper, and reinforced with synthetic resin to form a second electrode, which is removed from the second model. The electrodes are then used to erode respective opposite sides of an erosion body to form the spare parts.

11 Claims, 3 Drawing Sheets

METHOD FOR THE PRODUCTION OF DENTAL SPARE PARTS, SUCH AS TOOTH CROWNS- AND BRIDGES, BY MEANS OF SPARK EROSION

BACKGROUND OF THE INVENTION

The present invention is in a method for the production of dental spare parts, such as tooth-crowns and bridges, by means of spark erosion In this method a positive wax model is first fabricated, is then embedded into a casting mold and the wax is removed. Two form electrodes are prepared and the spare part is fabricated by means of spark erosion taking off material from an erosion body.

Such a method is described in the Deutsche Zahnärztliche Z 41, 525–526 (1986) under the title "Production of Metal Jacket Crowns Out of Full Material by Means of Spark Erosion". Pursuant to this method wax models of crown- or filling material [inlay material]are fabricated. The wax model is coated above and below the crown equator by a galvanic method with a copper layer having a thickness of about 1 mm. and the two copper molds, which can be separated in the area of the equator are lined with a reinforcing backing or rear construction. By means of the two form electrodes a metal molded blank is successively treated erosively. The two metal electrodes penetrate correspondingly into the erosive abrasion and form the dental spare piece of it. The accuracy of the spare piece to be eroded can be varied, especially in the area of its surface, by means of a modification of the abrasion speed. The article mentions that the spark erosion of such a spare part requires about an hour. The erosion time can be reduced by using a pre-formed metal body, serving as erosion body.

DE-PS 33 20 902 discloses a method for the production of tooth spare parts, especially casting fillings, part crowns or full crowns in which there is a precise fitting between the tooth frustrum and a spare part to be superimposed thereon. For this purpose in a multi-step procedure, a positive model of the tooth-frustrum is produced and the surface of the pre-fabricated tooth-surrogate to be fitted onto the tooth frustrum is adapted by means of an erosion procedure. Only very thin layers are eroded onto the pre-fabricated tooth spare part in the area of the posterior contact surface to the tooth frustrum.

EP-A2-0 225 513, to which U.S. Pat. No. 4,734,173 corresponds, describes a procedure and arrangement for the production of tooth spare parts. In that method, the tooth spare piece to be fabricated is produced directly by means of a spark erosion by means of two form electrodes, out of a full, not previously treated material. As discussed above, the erosive abrasion for the production of the tooth spare piece is very time-consuming.

SUMMARY OF THE INVENTION

An object of the present invention is to provide a method for the production of tooth spare parts by use of the spark erosion method, by which a multitude of different spare parts with a precise fitting in both the biting surface and the carrier body, is produced. The carrier body, for example, is put onto the tooth frustrum.

That objective is obtained by a method wherein the individual wax models of a multitude of spare parts to be produced are disposed on a carrier respectively and are placed onto a common support at a small distance from each other. The individual spare parts are disposed and arranged at a level above the support in such a way, that the widest horizontal cutting section of each spare part lies in one common equator plane. This arrangement is inserted into a casting frame. The areas between the individual spare parts are filled up to the equator plane with a forming mass, and an orientation pin, which runs vertical to the equator plane and projects thereover, is positioned in at least two interspaces. After the surface of the first so constituted model is cleaned, a silver coating, which serves as a separating and a conducting layer, is applied onto the cleaned surface and the silver layer is electroplated with a copper reinforcement. A stabilizing rear construction is applied onto the copper layer. The arrangement established in this way is formed out. The model obtained is separated out and is rotated by 180 degrees about an axis disposed in the equator plane. The rotated model is inserted into a casting frame and filled up with a hardening carrier mass. After the carrier mass hardens, the shaping out mass between the carriers is removed. A silver layer is applied onto the surface, which is obtained pursuant to the shaping out, and the silver layer is plated with a copper reinforcement. A stabilizing rear construction is applied onto the copper layer and the so formed model is shaped out above the equator plane. One model is oriented and inserted into the sleeve-head of an erosion device above the erosion body and subjected to an eroding action. The erosion body is rotated 180 degrees about an axis disposed in the equator plane. The other model is oriented and inserted into the sleeve-head above the rotated erosion body and subjected to an eroding. The remaining cross-pieces in the area of the equator plane from the spare parts are removed.

The described method provides the ability to fabricate a multitude of tooth spare parts economically and with a high degree of accuracy. A substantive step in the method is to dispose the positive models, which are generally of wax, onto a common carrier, so that casting molds can be produced and shaped out. For this purpose the individual spare parts are oriented in a common equator plane, that is in its widest horizontal cross section plane, this equator plane being the separation plane for the posterior erosion electrodes.

In an important step of the method the interspaces between the individual spare parts are filled out up to the equator plane, in order to produce first the upper electrode. In order to keep a remaining arrangement among the models for the fabrication of the electrodes during the individual steps of the procedure, one or several orientation pins are disposed vertically to the equator plane already when the interspaces between the individual tooth-spare part- wax models are filled up. Preferably the tooth spare parts are put onto the bottom of a tank, the lateral walls of which also form the casting frame.

Preferably an easily flowing mass of a silicone mixture is used as casting mass. When the silicone mixture hardens, the surface is cleaned of impurities, especially fats and oils, in order to coat the cleaned model eventually with a thin silver layer, which serves as a conducting layer for the posterior erosion electrode. In a subsequent procedure the silver layer is coated galvanically with a copper layer serving as a reinforcement. On the copper layer, contacts can be soldered at the rim towards the casting frame. When the copper layer has been formed, a further stabilizing rear construction, which may be of a synthetic resin, is applied. The entire construction is shaped out and the latest applied rear construction is milled or ground parallel to the equator plane or to the separation plane between the filling mass and the silver layer, so that this part can be inserted into and oriented in the sleeve-head of an erosion device.

For the fabrication of the second model, the first model is rotated 180 degrees about an axis disposed in the equator plane, and is inserted into the form, which is filled in the bottom area with a hardening carrier mass. When the carrier mass is hardened, the individual carriers of the wax models, which stand up, and the filling material between the individual carriers, which is cast between the individual carriers for the production of the first electrode, are removed so that now the individual models sit in a fixed assignment to each other in the casting mold.

The arrangement is again coated with a silver layer and eventually is coated galvanically with a copper reinforcement. Additionally, the electric connections are attached and a stabilizing rear construction is applied onto the copper layer. After the shaping-out the upper part can be removed and when the upper side is milled, it can be inserted as a second electrode into the sleeve-head of an erosion machine by means of orientation pins. Then the erosion block is eroded from both sides with the one or the other electrode until the electrodes rest in one of the planes, which originally corresponded to the equator plane and the tooth spare parts are obtained. Adjacent spare parts may still be connected to each other by cross pieces, which are removed. Since originally the orientation pins had been cast into the models, there is the possibility to insert the two electrodes oriented into the erosion machine in the framework of the erosion process.

Preferably the areas between the individual tooth spare parts disposed on the carriers are filled up with a shaping-out mass made up of a silicone-caoutchouc (rubber) which flows especially evenly into the interspaces of the individual spare parts and does not arch up along the individual spare parts.

For the formation of the respective stabilizing rear construction and of the carrier mass, in which the individual wax models are rotated by 180 degrees about the equator plane for the fabrication of the second model, a cold-hardening casting resin has proven to be especially suitable. Such resins generate little or no stress or tensions during and after hardening.

The dental parts made up of wax and the surface of the shaping-out mass between the carrier can be coated especially evenly, even with the corner areas, with a sprayed-on silver layer. The thickness of the layer should be between 2 and 100 $\mu$m, preferably 2 and 5 $\mu$m. In the contrast the stabilizing copper layer, which is applied galvanically, should preferably provide a thickness of 1 mm., and at least of 0.5 mm., to insure sufficient stability.

DESCRIPTION OF PREFERRED EMBODIMENT

Figure 1:
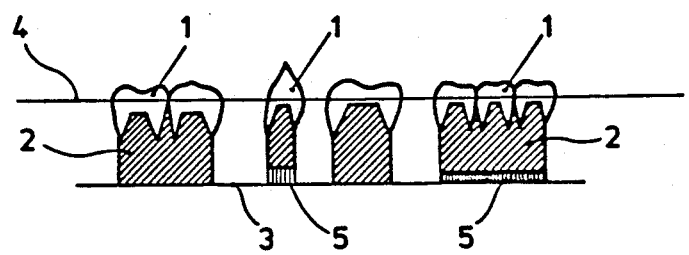
FIG. 1 shows a support, on which individual dental models are disposed on carriers.

For the production of a first erosion electrode, individual wax models 1, which are superimposed onto gypsum bodies 2 (carriers), are disposed on a support 3. On each wax model 1 an equator plane 4, which corresponds to the widest horizontal cross-sectional plane of that model, is drawn in. The individual spare parts are arranged with respect to each other on the support in such a way, that the individually drawn equator lines are oriented in a common equator plane. If necessary, individual gypsum bodies can be underfilled with spaced blocks 5, in order to align the individual equator lines in a common equator plane 4.

Figure 2:
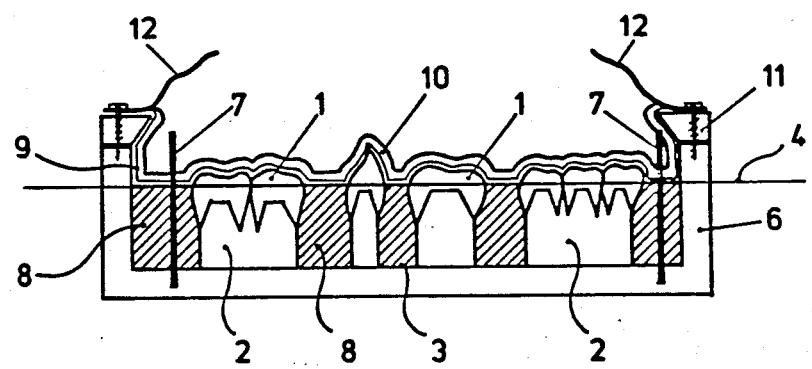
FIG. 2 shows the arrangement of FIG. 1 in a casting tank.

The oriented spare parts then are inserted with their support 3 into a casting frame 6 which may be fashioned like a tank, as shown in FIG. 2. Instead of a separate support 3 it is possible to superimpose the gypsum bodies or carriers 2 with the wax models 1 directly onto the bottom of the frame 6 as a support and to orient it in the equator plane 4. In the marginal area of the frame 6 two fitting pins 7 are inserted vertically into the support 3, and determine the orientation of the model and the posterior insertion into the erosion head.

When the fitting pins 7 are inserted, the interspace between the individual gypsum bodies 2 and between the gypsum bodies 2 and the frame 6 is hardened out up to the height of the equator by means of a shaping-out mass 8, which is preferably a silicone. Such a shaping-out mass 8 of silicone has sharp limitations or edges formed in the equator plane 4 at the projecting wax models. When the surface of the so called first model has been cleaned of impurities, especially, of deposited silicone oil or other fats, a silver layer 9 having a thickness of around 10 $\mu$m is sprayed onto the surface of the wax models 1 and of the silicone or shaping-out mass 8 in the equator plane 4. Eventually a thick, stabilizing copper layer 10 having a thickness of about 0.7 mm. is electroplated onto the silver layer 9. The plating is carried out during several hours, the starting voltage being very low. The casting frame 6 thus also serves for mounting the carriers during plating.

As shown in FIG. 2, on the rim of the frame 6 an additional frame 11 is superimposed, providing an edge, which projects inwardly of frame 6 and to which connection contacts 12, which contact the silver layer 9 and the copper layer 10, are fastened. The silver layer 9 serves as a separating and conducting layer and forms the erosion and contact surface of the erosion head to be produced.

Figure 3:
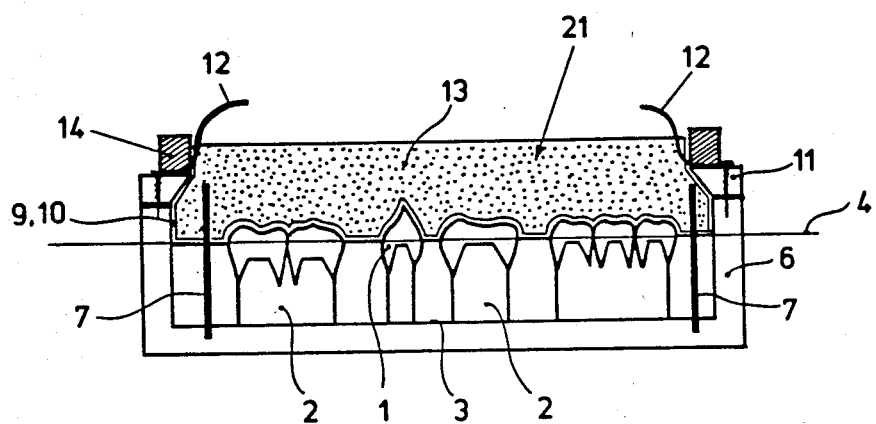
FIG. 3 shows an arrangement of FIG. 2 with an additional rear construction.

In order to stabilize the silver layer 9 and the copper layer 10, a stabilizing rear construction 13, for example of a synthetic resin, is cast on as shown in FIG. 3. An additional casting frame 14 increases the filling height for this rear construction 13. Finally the upper side of the rear construction 13 is ground parallel to the equator plane 4, before this first electrode 21 is taken out of the frame 6. After the electrode has been cleaned with a brush, it can be inserted into a sleeve-head 15 of an erosion device, as can be seen in FIG. 5.

Figure 4:
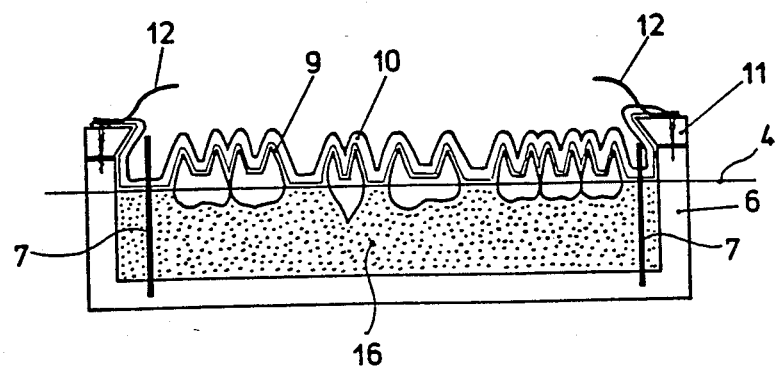
FIG. 4 shows the wax models in a rotated disposal.
Figure 6:
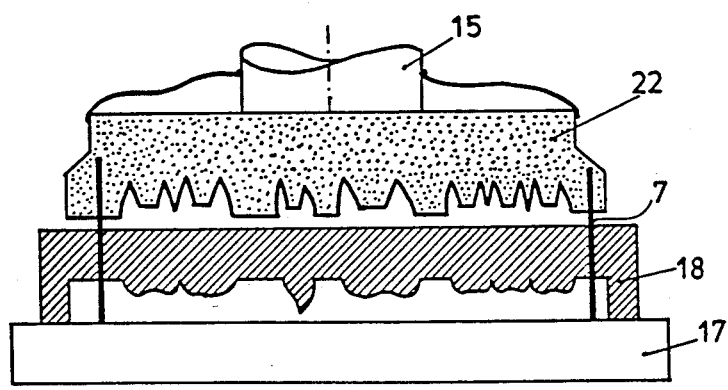

For the fabrication of a second electrode 22, which in FIG. 6 corresponds in its form to the form of the wax models disposed in the lower areas of the equator plane, the model as shown in FIG. 3 is taken out of the frame 6 with the individual wax models 1, put onto the gypsum bodies 2 and with the shaping-out mass 8, is rotated by 180 degrees and is reinserted into the frame 6. Before the model is inserted into the frame 6, the galvano frame is filled with a carrier mass 16, as shown in FIG. 4. Here the fitting pins 7 allow an oriented insertion of the model into the frame. When the carrier mass 16 is hardened out, the raised gypsum elements 2 and the shaping-out mass 8 are removed from the wax models 1. Thus an arrangement is obtained, as shown in FIG. 4, in which the individual wax models now turned by 180 degrees project over the equator plane 4. If need be the surface is cleaned and first a silver layer 9 is applied according to the method shown in FIG. 2 and eventually a reinforcing copper layer 10 is electroplated and connecting contacts 12 are fastened. Finally a stabilizing rear construction is applied onto the copper layer and the upper side of the rear construction is ground parallel to the equator plane 4. This second electrode 2 can be oriented in an erosion device and can be inserted by means of fitting pins 7.

Figure 5:
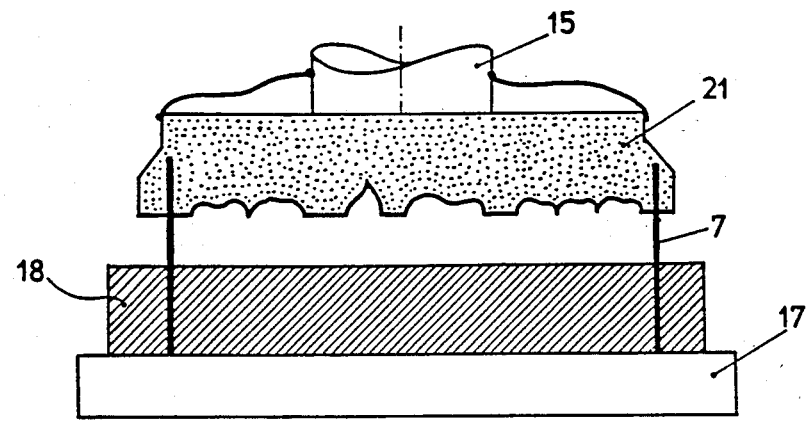
FIGS. 5 and 6 show two erosion heads fabricated in an erosion device.
Figure 7:
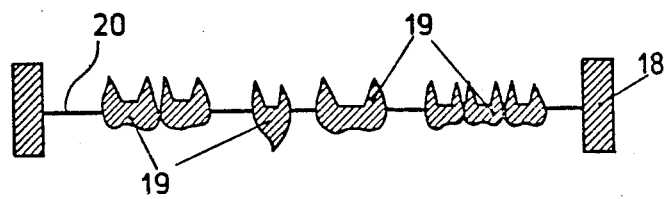
FIG. 7 shows the eroded tooth spare parts, which are connected to each other.

FIG. 5 shows an arrangement of an erosion device with an erosion table 17, onto which an erosion body 18, for example a metal body made up of a nickel-chrome alloy or of an alloy containing special steel, is superimposed. The erosion body 18 is eroded with the first electrode 21, until the shape of the electrode, which corresponds to the area of the spare tooth parts above the equator plane, is reproduced in the erosion body 18. The erosion body 18 is removed from the erosion device, is rotated 180 degrees and is reinserted, as shown by FIG. 6. The counter side of the erosion body 18 can be eroded with the second electrode 22, so that the individual tooth spare parts 19 are completely imitated, as illustrated in FIG. 7. The individual parts 19 are connected to each other by thin bars 20, so that they can be separated from each other very easily. It is possible as well to treat the erosion body 18 from both sides at a time.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for the production of dental spare parts comprising:
    disposing individual positive wax models on carriers a small distance from each other in a casting frame in such a way, that the widest horizontal cutting plane of each positive wax model is situated in a common equator plane;
    filling areas between the individual positive wax models with a molding mass up to the equator plane to provide a first model;
    inserting in at least two interspaces respectively one orientation pin, said orientation pins being disposed vertically to the equator plane;
    cleaning a surface of the first model;
    forming a silver coating on the cleaned surface of the first model;
    electroplating the silver layer with a copper reinforcement;
    providing a stabilizing rear construction on the copper reinforcement to form a first electrode;
    finishing the first electrode and removing it from the casting frame;
    rotating the first model through 180 degrees about an axis disposed in the equator plane;
    inserting the rotated first model into a casting frame filled with a hardening carrier mass;
    detaching the carriers and the molding mass after the hardening of the carrier-mass to provides a second model;
    forming a silver layer on a surface of the second model;
    electroplating the silver layer with a copper reinforcement layer;
    providing a stabilizing rear construction on the copper layer to provide a second electrode;
    finishing the second electrode and separating it from the casting frame;
    eroding a first surface of a body with the first electrode; eroding a second surface of the body, opposed from said first surface, with the second electrode; and
    removing remaining cross-pieces from the resulting eroded body in the area of the equator-plane to provide the spare parts.

2. The method of claim 1 wherein the molding mass is silicone caoutchouc.

3. The method of claim 1 wherein the stabilizing rear construction is of a low temperature hardenable casting resin.

4. The method of claim 1 wherein the carrier mass is of a low temperature hardenable casting resin.

5. The method of claim 1 wherein at least one of the silver layers is sprayed on.

6. The method of claim 5 wherein the at least one silver layer has a thickness of about 2 to 100 $\mu$m.

7. The method of claim 6 wherein the layer has a thickness of 2 to 5 $\mu$m.

8. The method of claim 1 wherein at least one of the copper layers is a dense copper layer and has a thickness of at least 0.5 mm.

9. The method of claim 8 wherein the least one copper layer has a thickness of about 1 mm.

10. The method of claim 1 wherein the wax models are disposed on a carrier made of gypsum.

11. The method of claim 1 wherein said individual positive wax models and said carriers are disposed on a common support which is inserted into said casting frame.

* * * * *